Oct. 8, 1957 A. NORMAN Plant Pat. 1,650
ROSE PLANT
Filed Nov. 6, 1956
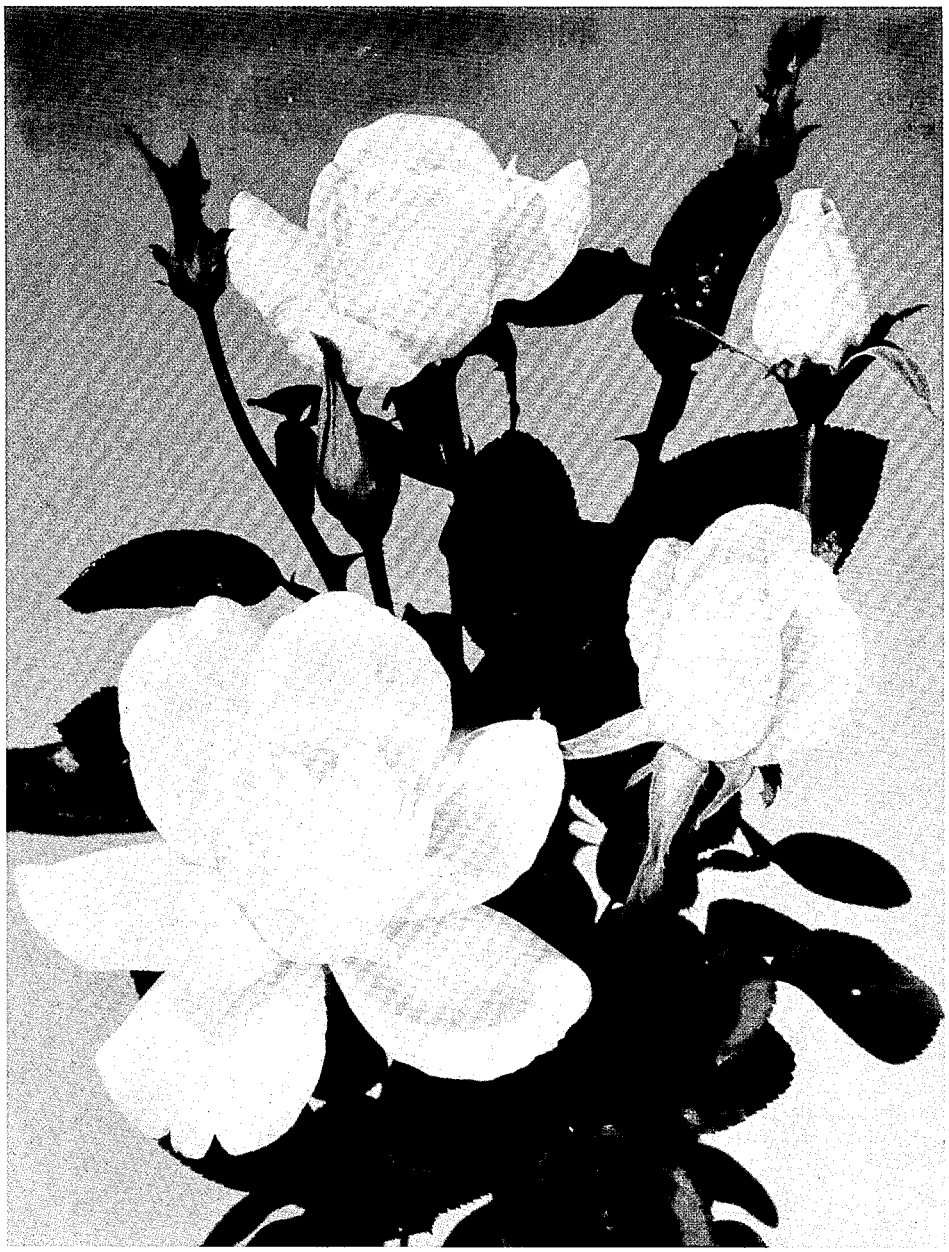
Inventor.
Albert Norman
By: Robert Cobb
Attorneys.

United States Patent Office

Plant Pat. 1,650
Patented Oct. 8, 1957

1,650

ROSE PLANT

Albert Norman, Wisteria, Normandy, Surrey, England, assignor to Armstrong Nurseries, Inc., Ontario, Calif., a corporation of California Application November 6, 1956, Serial No. 620,779

1 Claim. (Cl. 47—61)

The present invention relates to a new and distinct variety of rose plant of the hybrid tea class, which was originated by me by crossing the variety "McGredy's Yellow" (unpatented) with the variety "Phyllis Gold" (unpatented). The primary objective of this cross was to produce a new rose variety which combines the best characteristics of its parents. This objective was fullly achieved, as evidenced by the following unique combination of dominant features which are characteristic of the new variety:

(1) A free-branching habit, inherited from the parent variety "Phyllis Gold," causes the plant to flower more freely than the variety "McGredy's Yellow";

(2) The foliage of the new variety is more abundant than that of either parent;

(3) The wood and foliage of the new variety have the attractive appearance of "McGredy's Yellow," but a deeper color and a more glossy appearance have been inherited from "Phyllis Gold";

(4) The stems of the new variety are firm and upright, as in "McGredy's Yellow," but have a more branching habit which has been inherited from "Phyllis Gold"; and (5) The deeper color of the flowers of "Phyllis Gold" has been inherited by the new variety, but instead of having paler outside petals such as are characteristic of that parent, the new variety has true-colored outside petals as found in "McGredy's Yellow," and as a result, the flowers of the new variety appear brighter in color than those of either parent.

In comparison with the seed parent, "McGredy's Yellow," the blooms of my new variety are a brighter shade of yellow; the new variety develops side shoots while the terminal buds are forming, whereas in "McGredy's Yellow" the development of side shoots is usually deferred until the terminal buds are more mature; and the foliage of the new variety is a glossy olive green, whereas that of "McGredy's Yellow" is more bronzy.

As compared with the pollen parent, "Phyllis Gold," the stems of my new variety are upright, whereas those of this parent are more pendulous; the flowers are a bright yellow color throughout, whereas those of this parent are lighter at the edges; and the foliage of the new variety is large and abundant, with consequent good coverage of the plant, whereas that of this parent is less abundant and substantially smaller in size.

The foregoing characteristics and distinctions definitely differentiate the new variety from its parents, as well as from all other varieties of which I am aware, and asexual reproduction of the new variety by budding, as performed in England, and also at Ontario, California, U. S. A., shows that said characteritsics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"):

Type: Bush; outdoor; seedling; for cut flowers and for garden decoration.

Class: Hybrid tea.

Breeding: Seedling.

*Seed parent.*—"McGredy's Yellow."

*Pollen parent.*—"Phyllis Gold."

Propagation: Holds its distinguishing characteristics through succeeding propagations by budding.

*Flower*

Locality where grown and observed: Ontario, California, U. S. A.

Flowers borne: Usually singly, but sometimes 2 or 3 to stem; on strong, long stems.

Quantity of bloom: Free, outdoors.

Continuity: Nearly continuous during growing season.

Fragrance: Moderate. Nature—tea.

Bud:

*Peduncle.*—Long; heavy; erect; smooth; numerous gland-tipped cilia; some prickles. Color—between Courge Green, Plate XVII (Ridgway) and Biscay Green, Plate XVII (Ridgway), overlaid with near Prussian Red, Plate XXVII (Ridgway) on side exposed to the sun.

*Before calyx breaks.*—Size—medium. Form—medium length; from pointed to ovoid; with foliaceous appendages and gland-tipped cilia on the surface of the bud; usually with stout, much-cut foliaceous parts extending beyond the tip of the bud equal to ¼ or more of its length.

*As calyx breaks.*—Color—between Aureolin, Plate 3/2, p. 3 (Wilson) and Lemon Yellow, Plate 4/2, p. 4 (Wilson).

*Sepals.*—Inner surface with fine, woolly tomentum; margins of alternate sepals lined with fine woolly tomentum; others lined with gland-tipped cilia and some hairs.

*As first petal opens.*—Size—average. Form—medium length; urn-shaped. Color: outside—near Canary Yellow, Plate 2/2, p. 2 (Wilson), with area at base of petal equal to approximately ⅕ of petal near Lemon Yellow, Plate 4/1, p. 4 (Wilson); inside—near Canary Yellow, Plate 2/2, p. 2 (Wilson), with area at base of petal equal to approximately ⅕ of petal near Lemon Yellow, Plate 4/1, p. 4 (Wilson).

*Opening.*—Opens up well; is not retarded from opening by cold, hot, wet or dry weather.

Bloom:

*Size (when fully open).*—From average to large; from 4 inches to 5 inches.

*Petalage.*—Double; from 28 to 34 petals, plus 8 to 12 petaloids; arranged regularly.

*Form.*—High-centered at first, but becoming open later; petals being at first cupped, with lateral margins reflexed from ¼ to ½ of petal length, and with apex sometimes reflexed slightly from ⅛ to ¼ of petal length; becoming later at maturity flat-cupped, with lateral margins reflexed ½ or more of petal length, and with apex sometimes reflexed ¼ or more of petal length.

Petals:

*Texture.*—Medium thickness; with inside slightly shiny and outside from shiny to satiny.

*Shape.*—Outside—broadly obovate, with apex flat, and sometimes with one or two notches. Intermediate—obovate, with apex from rounded to flat, and sometimes with one or two notches. Inside—narrowly obovate; irregular; with apex rounded, and with one or two notches.

This description of a newly opened flower was made from a rose grown outdoors in the month of September, at Ontario, California, U. S. A.:

*Color.*—Outer petal: outside surface—near Mimosa Yellow, plate 602/2, p. 143 (Wilson), with area at base of petal near attachment near Canary Yellow, Plate 2, p. 2 (Wilson); inside surface—between Mimosa Yellow, Plate 602/2, p. 143 (Wilson) and Canary Yellow, Plate 2/2, p. 2 (Wilson), with area at base of petal near attachment near Canary Yellow, Plate 2, p. 2 (Wilson). Intermediate petal: outside surface—near Mimosa Yellow, Plate 602/2, p. 143 (Wilson), with area at base of petal near attachment near Canary Yellow, Plate 2, p. 2 (Wilson); inside surface—between Mimosa Yellow, Plate 602/2, p. 143 (Wilson) and Canary Yellow, Plate 2/2, p. 2 (Wilson), with area at base of petal near attachment near Canary Yellow, Plate 2, p. 2 (Wilson). Inner petal: outside surface—near Mimosa Yellow, Plate 602/2, p. 143 (Wilson), with area at base of petal near attachment near Canary Yellow, Plate 2, p. 2 (Wilson); inside surface—between Mimosa Yellow, Plate 602/2, p. 143 (Wilson) and Canary Yellow, Plate 2/2, p. 2 (Wilson), with area at base of petal near attachment near Canary Yellow, Plate 2/2, p. 2 (Wilson).

This description was made from a rose that was open for 3 days outdoors in the month of September, at Ontario, California, U. S. A.:

*Color.*—Outer petal: outside surface—between Mimosa Yellow, Plate 602/3, p. 143 (Wilson) and Canary Yellow, Plate 2/3, p. 2 (Wilson), with area at base of petal near attachment near Canary Yellow, Plate 2/1, p. 2 (Wilson); inside surface—between Mimosa Yellow, Plate 602/2, p. 143 (Wilson), and Canary Yellow, Plate 2/3, p. 2 (Wilson). Inner petal: outside surface—between Mimosa Yellow, Plate 602/3, p. 143 (Wilson) and Canary Yellow, Plate 2/3, p. 2 (Wilson), with area at base of petal near attachment near Canary Yellow, Plate 2/1, p. 2 (Wilson); inside surface—between Mimosa Yellow, Plate 602/2, p. 143 (Wilson) and Canary Yellow, Plate 2/3, p. 2 (Wilson).

*General color effect.*—Newly opened flower—between Mimosa Yellow, Plate 602/1, p. 143 (Wilson) and Canary Yellow, Plate 2/2, p. 2 (Wilson). 3-days open—between Mimosa Yellow, Plate 602/3, p. 143 (Wilson) and Canary Yellow, Plate 2/3, p. 2 (Wilson), with near Mimosa Yellow, Plate 602, p. 143 (Wilson) toward center of bloom.

*Behavior.*—Drop off cleanly; not particularly affected by cold, hot, wet or dry weather.

*Flower longevity.*—On bush in garden—3 days in September. Cut roses grown outdoors and kept at living-room temperatures—3 or 4 days in September.

*Reproductive organs*

Stamens: Many; arranged regularly about pistils; a few mixed with petaloids.

Filaments: Medium lengths; from 7 to 10 mm. in length; most with anthers. Color—between Lemon Yellow, Plate 4/1, p. 4 (Wilson) and Buttercup Yellow, Plate 5/2, p. 5 (Wilson).

Anthers: Medium size; all open approximately at once. Color: upper side—margins near Indian Yellow, Plate 6/2, p. 6 (Wilson), with remainder near Aureolin, Plate 3/2, p. 3 (Wilson); under side—margins near Indian Yellow, Plate 6/2, p. 6 (Wilson), with remainder near Aureolin, Plate 3/2, p. 3 (Wilson).

Pollen: Moderate. Color—near Buttercup Yellow, Plate 5/2, p. 5 (Wilson).

Pistils: Many; approximately 90 in number.

Styles: Moderately even; average length; from 5 to 8 mm. in length; average caliper; bunched. Color—upper ½ of Style between Blood Red, Plate 820, p. 166 (Wilson) and Currant Red, Plate 821/2, p. 167 (Wilson); lower ½ of style near Uranium Green, Plate 63/3, p. 63 (Wilson).

Stigma: Color—near Straw Yellow, Plate 604/2, p. 67 (Wilson).

Ovaries: Most enclosed in calyx, but some protruding from calyx.

Hips: From short to average length; from flat to globular; smooth; walls thick and fleshy. Color (⅔ mature)—near Oil Yellow, Plate V (Ridgway).

Sepals: Permanent; from medium length to long; recurved. Color: inside—between Courge Green, Plate XVII (Ridgway) and Biscay Green, Plate XVII (Ridgway); masked by white woolly tomentum; outside—between Courge Green, Plate XVII (Ridgway) and Biscay Green, Plate XVII (Ridgway).

Seeds: From few to average number; from 4 to 13 in number; from small to medium size.

*Plant*

Foliage:

*Leaves.*—Compound of usually 5 to 7 leaflets; abundant; medium size; leathery; semi-glossy.

*Leaflets.*—Shape—ovoid, with apex acute. Base—round. Margin—simply serrate.

*Color.*—Mature: upper surface—between Forest Green, Plate XVII (Ridgway) and Deep Dull Yellow-Green (1), Plate XXXII (Ridgway); under surface—near Chromium Green, Plate XXXII (Ridgway). Young: upper surface—between Dark Mineral Red, Plate XXVII (Ridgway) and Dark Indian Red, Plate XXVII (Ridgway); under surface—between Mineral Red, Plate XXVII (Ridgway) and Indian Red, Plate XXVII (Ridgway).

*Rachis (the supporting stem of the compond leaf).*—Average size. Upper side—grooved; with many stipitate glands on edges. Under side—with stipitate glands, and from 2 to 4 prickles.

*Stipules.*—Medium length; medium width; with medium length points turning out at an angle of more than 45°.

*Disease resistance.*—Average resistance to mildew as compared with other varieties grown under comparable cultural conditions, at Ontario, California, U. S. A.

Growth:

*Habit.*—Bushy; upright; much-branched.

*Growth.*—Vigorous.

*Canes.*—Medium caliper.

*Main stems.*—Color—between Yellowish Oil Green, Plate V (Ridgway) and Oil Green, Plate V (Ridgway). Large prickles—from several to many; medium length; hooked slightly downward; with moderately long, narrow base; color—between Light Drab, Plate XLVI (Ridgway) and Light Grayish Olive, Plate XLVI (Ridgway). Small prickles—several; color—between Light Drab, Plate XLVI (Ridgway), and Light Grayish Olive, Plate XLVI (Ridgway). Hairs—none.

*Branches.*—Color—near Light Elm Green, Plate XVII (Ridgway). Large prickles—from several to many; medium length; hooked slightly downward; with moderately long, narrow base; color— between Russet, Plate XV (Ridgway) and Cinnamon-Brown, Plate XV (Ridgway). Small prickles—several; color—near Russet, Plate XV (Ridgway). Hairs—none.

*New shoots.*—Color—between Mineral Red, Plate XXVII (Ridgway) and Indian Red, Plate XXVII (Ridgway). Large prickles—several; medium length; hooked slightly downward; with moderately long, narrow base; color—near Hydrangea Red, Plate XXVII (Ridgway). Small prickles—from few to several; color—near Hydrangea Red, Plate XXVII (Ridgway). Hairs—none.

I claim:

A new and distinct variety of rose plant of the hybrid tea class, substantially as herein shown and described, characterized particularly as to novelty by its free-branching and consequent free-flowering habit, abundant foliage, attractive deep-colored and glossy wood and foliage, firm and upright stems, and the distinctive bright yellow color of its flowers, with uniform coloring of the flower petals throughout the flowers.

No references cited.